(12) United States Patent
Galizia

(10) Patent No.: US 10,316,892 B2
(45) Date of Patent: Jun. 11, 2019

(54) HOT TESTING MACHINE, IN PARTICULAR OF THERMOPLASTIC POLYMERS, AND ASSOCIATED METHOD

(71) Applicant: ILLINOIS TOOL WORKS INC., Glenview, IL (US)

(72) Inventor: Giuseppe Galizia, Turin (IT)

(73) Assignee: Illinois Tool Works Inc., Glenview, IL (US)

( * ) Notice: Subject to any disclaimer, the term of this patent is extended or adjusted under 35 U.S.C. 154(b) by 168 days.

(21) Appl. No.: 15/478,624

(22) Filed: Apr. 4, 2017

(65) Prior Publication Data
US 2017/0284916 A1 Oct. 5, 2017

(30) Foreign Application Priority Data
Apr. 5, 2016 (IT) .................. 102016000034816

(51) Int. Cl.
*G01N 3/60* (2006.01)
*G01N 25/00* (2006.01)
(Continued)

(52) U.S. Cl.
CPC ........ *F16C 33/7886* (2013.01); *F16C 33/805* (2013.01); *G01N 3/42* (2013.01);
(Continued)

(58) Field of Classification Search
USPC ................................. 374/5, 57, 208, 141, 31
See application file for complete search history.

(56) References Cited

U.S. PATENT DOCUMENTS 3,774,440 A * 11/1973 Martinelli .............. G01N 25/04
374/52
3,868,221 A * 2/1975 Howard ................. G01N 33/26
374/102
(Continued)

FOREIGN PATENT DOCUMENTS

DE 102005023885 A1 12/2005

OTHER PUBLICATIONS

Anonymous: "Deflection Temperature and Vicat Testers Model 603 HDTM and 303 HDTW", Jan. 1, 2007 (Jan. 1, 2007), pp. 1-4, XP055310376, Retrieved from the Internet: URL:https://www.tiniusolsen.com/IManager/Download/815/59651/14623/1476398/EN/14623_1476398_1COI_138B-Heat-distortions.PDF [retrieved on Oct. 13, 2016].

(Continued)

*Primary Examiner* — Mirellys Jagan
(74) *Attorney, Agent, or Firm* — Lando & Anastasi, LLP

(57) ABSTRACT

Machine and method for hot testing test pieces made of a thermoplastic polymer, in which the test pieces are immersed in a tank full of a heat transfer liquid which is heated; a fan generates, immediately above the tank, an air flow to carry away volatile substances emitted by the tank and the air flow is made to pass through a filtering cartridge housed removably inside a first chamber delimited by a casing, which is provided with an inlet opening, that faces towards the tank and is arranged flush with or immediately above an upper perimetral edge of the tank; the air flow is made to pass sequentially through at least three filtering elements, which are arranged hydraulically in series, including: a pre-filter; at least one activated carbon filter; and a HEPA filter; an hour counter signals when the time has come to replace the filtering cartridge.

11 Claims, 3 Drawing Sheets

(51) Int. Cl.
  *G01K 1/00*   (2006.01)
  *F16C 33/78*  (2006.01)
  *F16C 33/80*  (2006.01)
  *G01N 3/42*   (2006.01)
  *G01N 25/04*  (2006.01)

(52) U.S. Cl.
  CPC ......... *G01N 25/04* (2013.01); *G01N 2203/02* (2013.01); *G01N 2203/0202* (2013.01); *G01N 2203/0226* (2013.01)

(56) References Cited

U.S. PATENT DOCUMENTS

| | | | | |
|---|---|---|---|---|
| 4,059,983 | A * | 11/1977 | Fritzsche | G01N 11/16 374/47 |
| 6,671,631 | B2 * | 12/2003 | Potyrailo | G01N 25/16 324/71.1 |
| 7,703,742 | B2 * | 4/2010 | Heim | F16K 99/0001 239/597 |
| 7,716,987 | B2 * | 5/2010 | Sathish | G01N 25/72 250/341.1 |
| 2009/0034580 | A1 * | 2/2009 | Lin | G01N 25/22 374/36 |
| 2011/0103425 | A1 * | 5/2011 | Alpeter | G01N 3/14 374/49 |
| 2016/0153921 | A1 * | 6/2016 | Al-Enezi | G01N 25/04 374/22 |

OTHER PUBLICATIONS

Italian Search Report and Written Opinion from corresponding Italian Application No. ITUA20162309 dated Oct. 17, 2016.

* cited by examiner

US 10,316,892 B2

HOT TESTING MACHINE, IN PARTICULAR OF THERMOPLASTIC POLYMERS, AND ASSOCIATED METHOD

PRIORITY CLAIM

This application claims priority from Italian Patent Application No. 102016000034816 filed on Apr. 5, 2016, the disclosure of which is incorporated by reference.

TECHNICAL FIELD OF THE INVENTION

The present invention concerns a hot testing machine for carrying out tests on the heat resistance of plastic materials, especially thermoplastic polymers, by detecting the deflection and/or deformation in the hot state of suitable test pieces made of the plastic material being tested.

PRIOR ART

As is known, for some applications, for example in the automotive industry, it is required that the plastic materials sold be accompanied by a declaration certifying their thermomechanical characteristics, in particular, their deflection and deformation under predetermined test conditions. Accordingly, numerous international standards exist which dictate the test conditions for plastic materials, such as the standards 3 ISO (75 part 1 and 2, 306) and 2 ASTM (D648 and D1525) respectively for HDT tests (Heat Deflection Temperature) and Vicat softening tests (VST).

Specifically, in the HDT test one measures the stress induced on a test piece subjected to a flexural load at 3 points. For this, the test piece is subjected to a load of predetermined value; it is then heated gradually and in a controlled manner (2° C. per minute) until reaching a predetermined deflection (0.25 rum for the ASTM test or a value between 0.32 and 0.36 mm for the ISO test). The temperature value at which this deflection is reached represents the HDT value.

In the Vicat test, or softening test, on the other hand, one measures the temperature at which a circular penetrator ("indenter") with a cross section of 1 mm$^2$, subjected to a predetermined load (weight), penetrates by 1 rum into the test piece.

For the performance of such tests, as set forth by the standard, a test piece is mounted appropriately on a support and immersed in a tank containing heating means (such as appropriate electrical resistors) and a liquid able to transfer heat from the heating means to the test piece under the indicated controlled conditions; the liquid usually consists of silicone oil, but the following description is applicable to any other type of heat transfer liquid.

Hence, for some time there have been available on the market test machines having a tank filled with a heat transfer liquid, typically silicone oil, which is heated and cooled by means of coils and fans so as to provide the required heating ramps of the test. The oil in the tank is moved by means of paddles in order to guarantee its uniform temperature at all points. In such machines, a test piece mounted on a support is immersed in the tank of oil and subjected to the action of the load, normally constituted by a head (in the HDT test) or a penetrator (in the Vicat test), a loading rod and a weight or group of weights. The deformation of the test piece is measured as a movement of a rod secured to the load or carrying the indenter; as soon as the rod moves by the value specified in the standard, the current temperature value of the oil is acquired, representing the HDT value or the softening value, depending on the type of test.

In the testing machines, therefore, the oil or other heat transfer liquid undergoes many cycles of heating (up to 290° C.) and cooling. This being in the majority of cases a fluid of organic nature, it may and in fact does emit, in the course of the heating and cooling cycles, vapors or in any case volatile organic substances, which may be harmful to health. Therefore, the vapors or volatile substances need to be carried away before they disperse into the surroundings.

For this purpose, the hot testing machines with an oil bath are currently placed under suction hoods connected to the treatment system of the plant.

Even so, such a solution has many drawbacks: it is bulky, costly, might not prevent the diffusion of vapors in the immediate proximity of the tank, even if they are then aspirated by the hood before they can disperse into the surroundings, and it is rather inflexible. In fact, if the machine needs to be moved or replaced, for example by one of larger dimensions, the hood needs to be adapted or moved, with substantial costs and difficulty, since the suction hood is part of the plant installation and is a unit separate from the testing machine and generally not dimensioned for use with it.

Moreover, the suction hoods generally aspirate large quantities of ambient air in order to be efficient. This means not only elevated operating costs, but also an elevated dilution of the volatile pollutants which are being aspirated, rendering them more difficult to eliminate afterwards from the air suctioned by the hood.

SUMMARY OF THE INVENTION

The purpose of the present invention is therefore to overcome the described drawbacks, in particular by providing a hot testing machine for carrying out tests on the heat resistance of plastic polymers which is independent of the plant installations and which at the same time is able to achieve an efficient and economical elimination of any volatile pollutants which may be emitted by the heat transfer liquid.

Another purpose of the invention is to ensure that this efficient elimination of volatile pollutants remains constant and reliable over the course of time.

Therefore, according to the present invention, a hot testing machine for testing the heat resistance of plastic materials and an associated method are provided, as defined in the appended claims.

BRIEF DESCRIPTION OF THE DRAWINGS

Further characteristics and advantages of the present invention will become clear from the following description of a non-limiting embodiment thereof, made purely for purposes of illustration, with reference to the appended figures of the drawings, in which.

DETAILED DESCRIPTION

Figure 1:
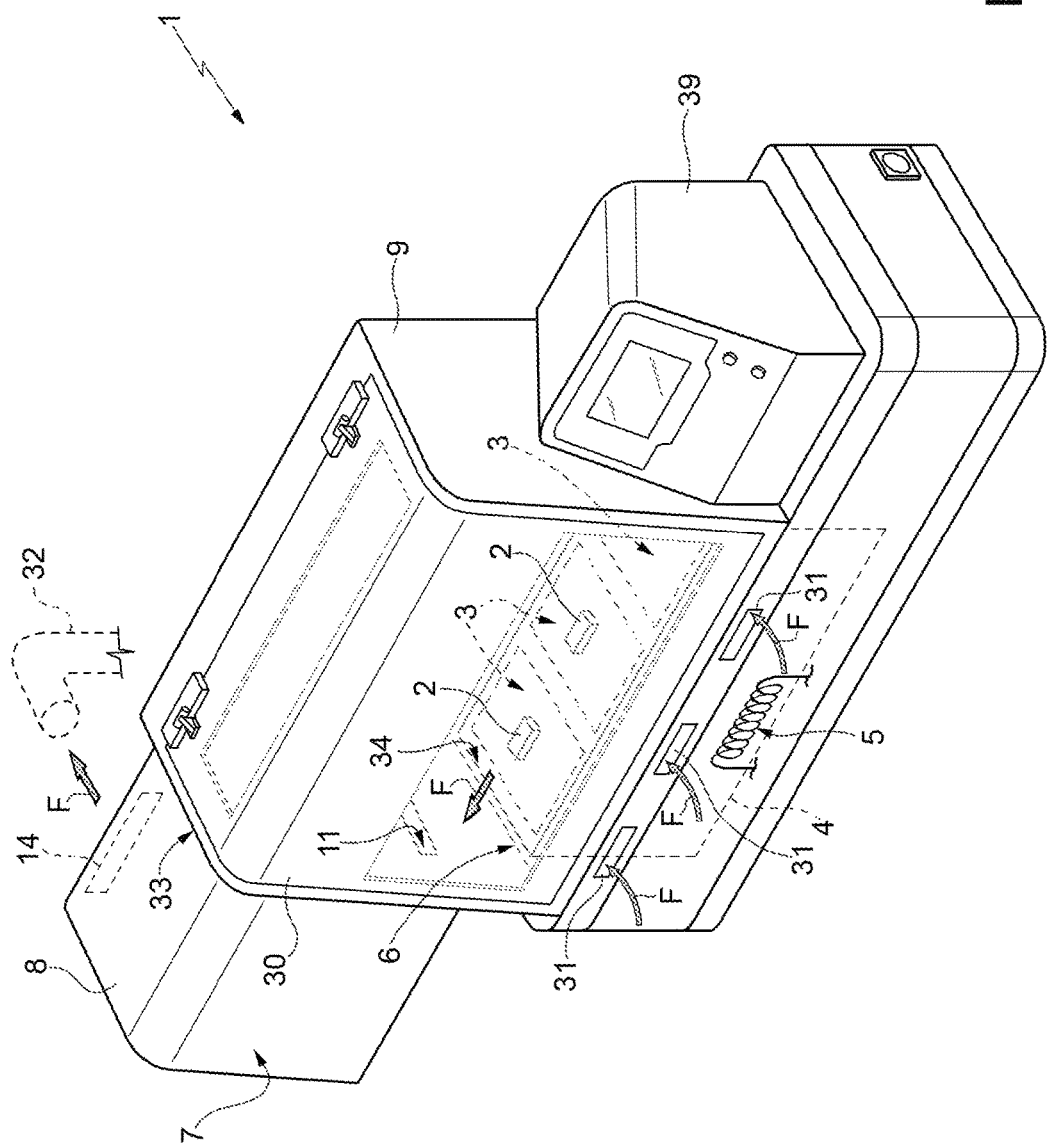
FIG. 1 illustrates schematically a perspective three-quarter front and top view of a hot testing machine for carrying out tests on the heat resistance of plastic polymers.
Figure 2:
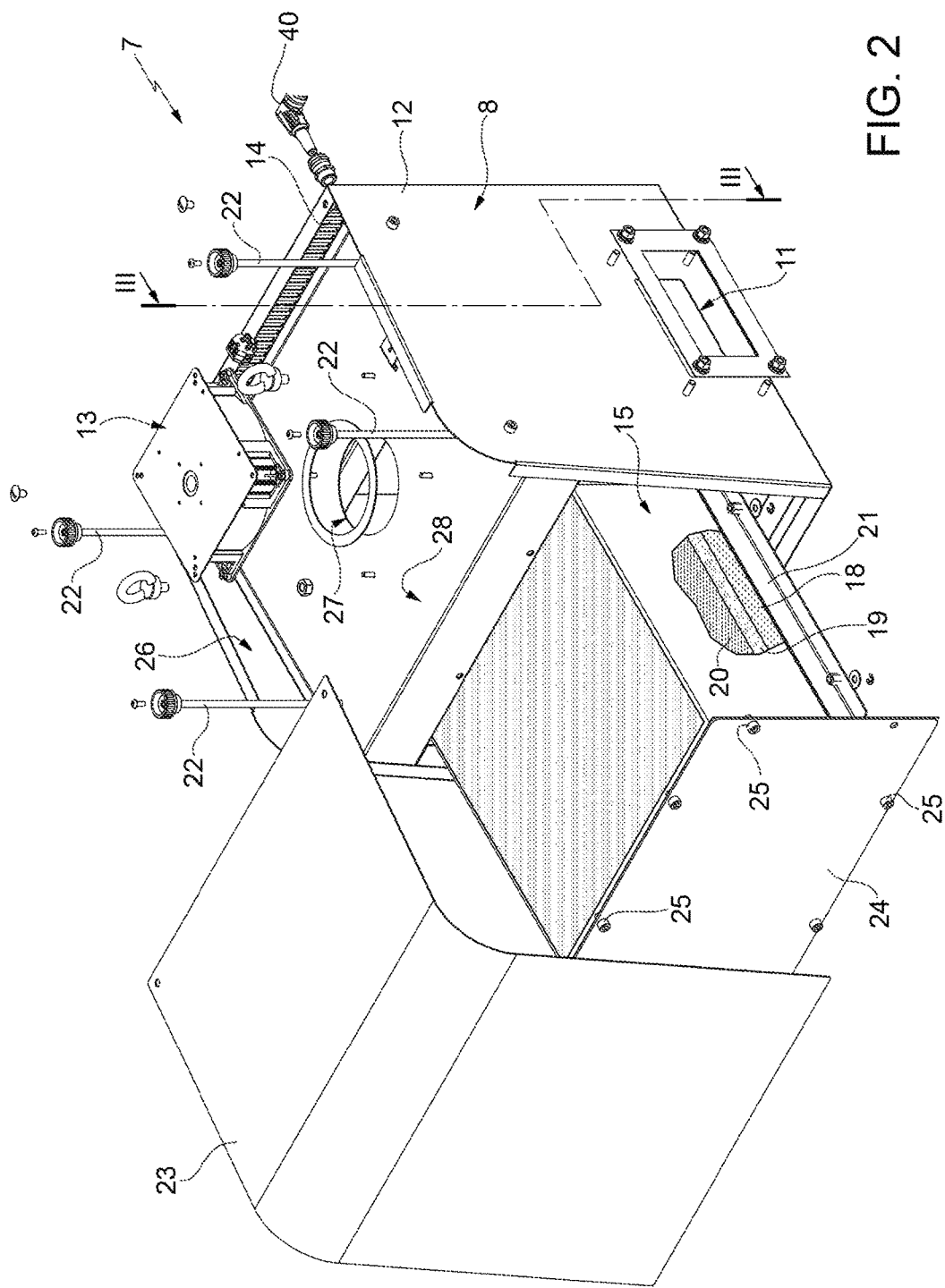
FIG. 2 illustrates schematically an exploded perspective view of a portion of the testing machine of FIG. 1.
Figure 3:
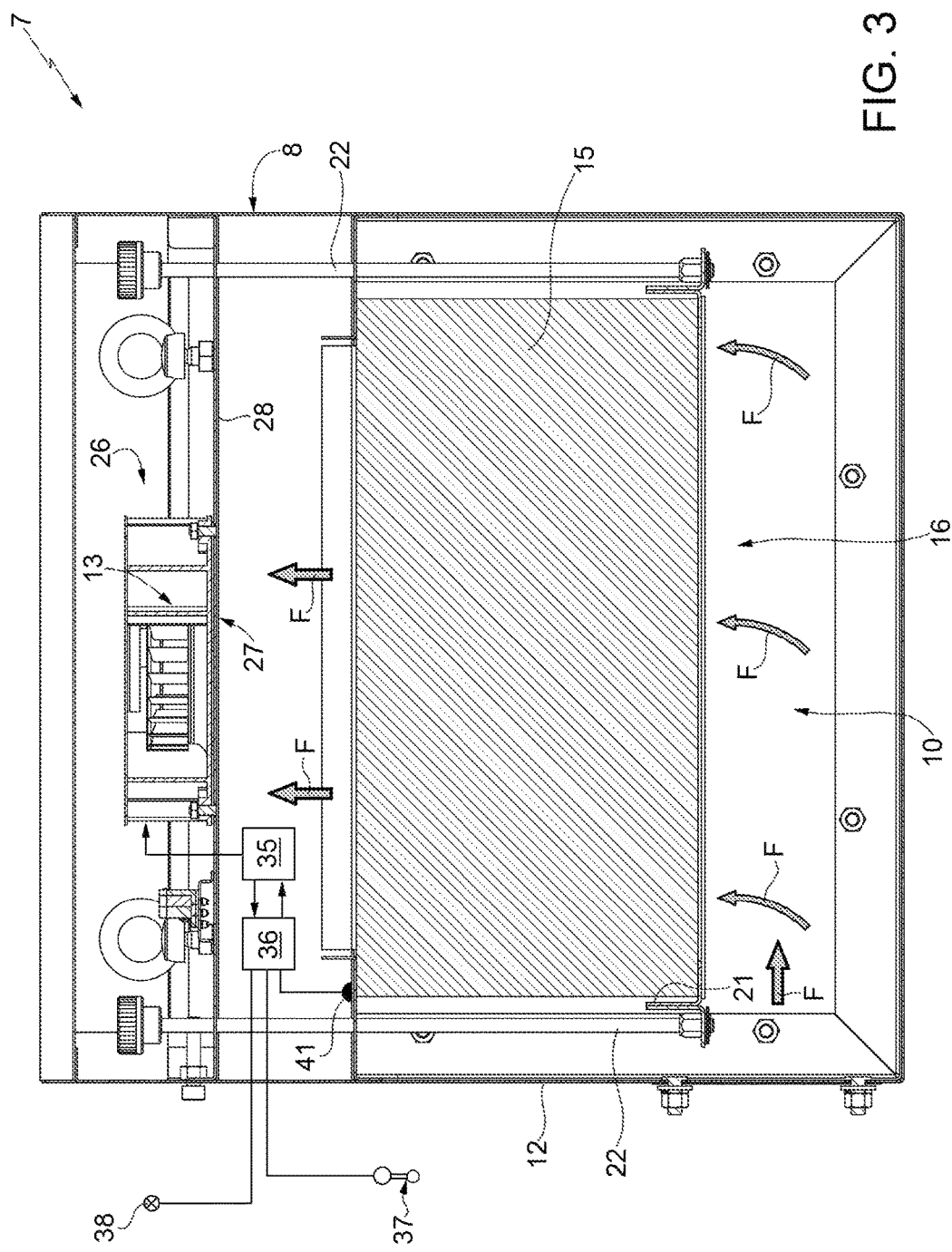
FIG. 3 is a schematic elevation view of the portion of machine of FIG. 2, sectioned along a plane III-III.

With reference to FIGS. 1 to 3, a hot testing machine for carrying out tests on the heat resistance of plastic polymers, especially thermoplastic polymers, is indicated as a whole by reference number 1; such tests, known as HDT (Heat Deflection Temperature) and Vicat tests, are performed according to ISO and ASTM or equivalent standards, being well known to the skilled person, and they consist in subjecting test pieces 2 made of the synthetic plastic material being tested to certain mechanical stresses by means of test stations 3, which are known and not illustrated in detail for simplicity, being indicated schematically by broken-line rectangles in FIG. 1.

The machine 1 illustrated without limitation in FIG. 1 comprises three test stations 3 arranged alongside each other in a longitudinal direction and designed to each receive at least one test piece 2 made of a plastic polymer which is to be tested, but more generally the testing machine 1 can comprise at least one and up to any number "n" test stations 2, being identical or of different type.

In any case, the testing machine 1 furthermore comprises a tank 4 which is open on top and is arranged immediately beneath the at least one test station 3; in the example of the machine of FIG. 1, the tank is beneath the three test stations 3. The tank 4 is designed to contain, during use, a heat transfer liquid, typically being composed of a silicone oil, and to selectively receive inside it, immersed in the heat transfer liquid, at least one test piece 2 which is carried by or arranged on a test station 3; in the nonlimiting example illustrated, the test stations 3 can be moved selectively in the vertical direction, in a known manner not described in detail for simplicity, within and outside of the tank 4, so as to selectively immerse one, several, or all of the test pieces 2 present on the machine 1 in the heat transfer liquid in order to carry out the tests.

Here and afterwards, we shall refer specifically, yet without sacrificing generality in this regard, to a silicone oil as the heat transfer liquid, but what is described may obviously apply to any other fluid possessing thermal conductivity.

The testing machine 1 further comprises a heating device 5 housed in the tank 4 or in the vicinity thereof; the heating device 5 is known and shall not be described in detail, for simplicity, and it is represented schematically as an electrical resistance coil; more generally, the heating device 5 also comprises means of movement of the heat transfer liquid, for example paddles, to ensure a uniform temperature within the tank 4, and means of cooling (such as coils circulating water, or other, such as Peltier effect cells) to enable a precision regulation of the heating ramps which are desired or required by the standards for the test pieces 2.

The tank 4 is bounded on the side toward the test stations 3 by an upper perimetral edge 6 which surrounds all of the test stations 3.

According to a first aspect of the invention, the testing machine 1 further comprises a suction and treating device 7 for volatile substances which may develop during use from the tank 4; typically, the silicone oil at the operating temperatures, which may normally reach temperatures greater than 200° C., can slowly degrade, releasing vapors and/or polluting substances such as formaldehyde, which collect above the edge 6.

The suction and treating device 7 is illustrated in detail in FIGS. 2 and 3 and it comprises a casing 8 which is fixed laterally to a supporting structure 9 arranged above the tank 4.

The casing 8 internally delimits a first chamber 10 (FIG. 3) and it has an inlet opening 11 to the chamber 10, which is arranged substantially flush with or immediately above the perimetral upper edge 6 of the tank 4 and is made through a lateral wall 12 of the casing 8 facing towards the tank 4.

The device 7 furthermore comprises: a suction fan 13, which is supported by the casing 8 above the chamber 10 and is connected hydraulically to the chamber 10 and to an outlet opening 14 made through the casing 8 itself; and a filtering cartridge 15, which is housed removably inside the first chamber 10 and is hydraulically interposed in a fluid-tight manner between the inlet opening 11 and the suction fan 13.

According to one aspect of the invention, the suction fan 13, the inlet opening 11 and the filtering cartridge 15 are configured, i.e. dimensioned, for the suction from immediately above the tank 4 and in conditions of substantially laminar motion of an air flow F at a predetermined flow rate such that to remove the vapors and/or contaminating substances which collect above the tank 4, in the present instance immediately above the edge 6. It has been discovered by experimentation that it is important for the air flow F, by which the stripping of the volatile polluting substances possibly emitted during use by the heat transfer liquid present in the tank 4 is carried out, to be generated and maintained in a continual manner under conditions of laminar motion, so as not to disturb the surface of the heat transfer liquid and to avoid mixing which might allow some of the volatile substances to escape the stripping.

As is illustrated in FIG. 3, the filtering cartridge 15 occupies only in part the first chamber 10, and occludes it immediately above the inlet opening 11, thus being interposed between the inlet opening 11 and the fan 13 with the respective outlet opening 14; in this way, a lower portion 16 of the chamber 10 in which the inlet opening 11 emerges laterally remains empty and the air flow F which is sucked up into the first chamber 10 by the fan 13 can be distributed uniformly in the portion 16 of the chamber 10, passing through the filtering cartridge 15 in a substantially vertical direction and then being directed through the fan 13 toward the outlet opening 14.

According to one aspect of the invention which is not secondary, the filtering cartridge 15 comprises (FIG. 2) at least three filtering elements 18, 19 and 20, which are arranged hydraulically in series with respect to the air flow F and comprise, considered in the direction of the air flow F: an at least grade G2 and preferably grade G4 pre-filter 18; at least one activated carbon filter 19; and a HEPA filter 20, preferably of grade H14. The activated carbon filter 19 is interposed between the pre-filter 18 and the HEPA filter 20.

Here and afterwards, the abbreviations "G2", "G4" and "H14" indicate the filtration capacity of the different air filters according to the international standards; for example, G2 stands for a filtration capacity for particles of dimensions between 65 and 80 microns (millionths of a rum); G4 means that 90% of particles with dimensions larger than 5 microns are held back by the filter; H14 means that 99.995% of the particles of dimensions larger than 0.3 microns are held back by the filter.

The filters 18 and 20 are of the "mini pleat" type, that is, they are formed by folded layers of nonwoven fabric made of glass fibers with diameter between 0.5 and 2 microns and they enclose in a pack the filter 19 made of active carbon granules. The filtering cartridge 15 further comprises a frame or carrying structure 21, preferably made of aluminum, which supports the filtering elements 18, 19 and 20.

By virtue of the frame 21, the filtering cartridge 15 is supported inside the casing 8 by at least four removable pins 22, and is extractable from the casing 8 like a drawer, as is well illustrated in FIG. 2, preferably in a direction perpendicular to a direction of admission of the air flow F through the inlet opening 11, as indicated by the arrow in FIG. 1.

According to the nonlimiting embodiment illustrated, the casing 8 has a substantially parallelepiped shape and is connected to the supporting structure 9 by the lateral wall 12, which bounds off one longitudinal end thereof. In front and on top, the casing 8 has a removable panel 23 of L-shape, whose removal allows access to the fan 13 and to a front panel 24 of the filtering cartridge 15, which is part of the frame 21 and secured in a fluid-tight manner to the casing 8, closing the chamber 10, by means of screws 25. By removal of the screws 25 and the pins 22, the filtering cartridge 15 can easily be taken out in the manner of a drawer from the casing 8 by acting on the front panel 24, which can have a handle, not illustrated for simplicity.

The suction fan 13 is housed inside a second chamber 26 of the casing 8, said second chamber being arranged above the first chamber 10 and being connected hydraulically to the first chamber 10 by means of a central hole or sleeve 27 which is made through/carried by a separation bulkhead 28 between the chambers 10 and 26 and forms an integral part of the casing 8; the chamber 26 is bounded at the top and in front by the removable panel 23, and therefore with the removal of the latter it is easily accessible for any maintenance work on the fan 13, which is supported by the bulkhead 28 on the opposite side of the chamber 10.

According to the preferred embodiment of the invention, the suction fan 13 is a centrifugal fan, which axially sucks up the air flow F from above the tank 4 and through the inlet opening 11 and the filtering cartridge 15 arranged in the first chamber 10 and discharges it radially into the second chamber 26 and towards the outlet opening 14, which is arranged laterally in relation to the second chamber 26 and is preferably arranged so as to be perpendicular to the inlet opening 11.

In the nonlimiting embodiment illustrated, the outlet opening 14 is defined by a rear grilled wall 29 of the chamber 26, opposite the front panel 24, and it is connected directly to the atmosphere.

According to this embodiment, the air flow F intended to remove the vapors and other volatile substances emitted by the heat transfer liquid contained in the tank 4 is configured in an open cycle: this means that the air flow F is sucked from the surroundings of the tank 4 and, after being purified by passing through the filtering cartridge 15, it is discharged into the atmosphere.

In the preferred embodiment illustrated, the supporting structure 9 above the tank 4 is a closed structure, sealed or not, which covers the tank 4 and the at least one test station 3; the supporting structure 9 is then equipped with an access door 30 to the tank 4 and to the at least one test station 3; the door 30 can be of the pivoting or sliding type and, in the case of an operation in open cycle, it can be provided with vents 31 (otherwise made through the supporting structure 9, for example on the side opposite the door 30 or at an upper window) to allow the air flow F to be suctioned from the outside.

According to another possible embodiment, the air flow F intended to remove the vapors and other volatile substances emitted by the heat transfer liquid contained in the tank 4 is configured in a closed cycle; in this case, the vents 31 are absent and the outlet opening 14 is connected in fluid-tight manner to a pipeline 32 which is in turn connected in obvious manner, not illustrated for simplicity, to the inside of the closed supporting structure 9, so as to continually recycle the air flow F between the tank 4 and the chamber 26.

The casing 8 of the suction and treating device 7, in the nonlimiting example illustrated, is supported in a cantilevered manner by a longitudinal end 33 of the supporting structure 9 arranged at a longitudinal end 34 of the tank 4 at which the inlet opening 11 is arranged, which inlet opening is configured as a horizontal vent arranged in parallel with the portion of edge 6 bounding the end 34.

According to a further aspect of the invention, the device 7 also comprises (FIG. 3) a control unit 35, for example of the microprocessor type or formed by a PLC, an hour counter 36, which can be a suitable register integrated in the control unit 35, a temperature sensor 37 arranged in the tank 4 or in the vicinity thereof, and an optical display 38, which can be a simple LED or, more generally, a screen able to display alphanumeric characters. Although control unit 35 and hour counter 36 are shown schematically in FIG. 3 as being units arranged within the device 7, more generally these are an integral part of an electronic control unit 39 to control the machine 1. Alternatively, these may be disposed anywhere in the machine 1 or inside the casing 8 and can be connected electrically to the control unit 39 for the purpose which shall be described.

The control unit 35, or the control unit 39 of which it may be an integral part, is designed or programmed to start the fan 13 and continually monitor its operation. Furthermore, if the fan 13 is shut off, the control unit 35/39 shuts off the machine 1 and the system goes into emergency mode, no longer being capable of suctioning. The control unit 35, or the control unit 39 of which it may be an integral part, is furthermore configured or programmed to additionally start, along with the fan 13, the hour counter 36, in the present case in response to a signal from the temperature sensor 37 indicating that a first predetermined threshold value has been exceeded, for example when the temperature of the bath of heat transfer liquid contained in the tank 4 exceeds 50° C. (or 65° C. or another temperature at which it is known that the heat transfer liquid begins to emit vapors or other volatile substances). The control unit 35/39 is also configured or programmed to stop the fan 13 and the hour counter 36 when the temperature detected by the sensor 37 is below the first predetermined threshold value, for example, when it drops below 50° C. At each start/stop cycle, the control unit 35/39 is also configured or programmed to compare the time value, for example the hours of operation of the fan 13, recorded on the hour counter 36 with a second predetermined threshold value, for example a time value memorized in a suitable register; and to activate the optical display 38 when the value recorded by the hour counter 36 is equal to a predetermined percentage of the second threshold value and/or is equal to or greater than the second threshold value.

For example, it has been established by experimentation that the efficiency of the filtering cartridge 15 remains acceptable for a certain time value, such as 1000 hours or more; the control unit 35/39, when the operating time value recorded by the hour counter 36 draws near, for example to 80% or 90% of the second predetermined threshold value of 1000 hours, for example, activates the optical display 38 to show a warning message, such as "the filtering cartridge is nearly used up" if the display 38 is of the alphanumeric type, or it lights up an LED, for example colored, if the optical display 38 consists of an LED or group of LEDs. Then, when the second threshold value of 1000 hours, for example, is reached or exceeded at the end of an on/off cycle of the fan 13, the control unit 35/39 activates the optical display 38 to show a second warning message, such as "the filtering cartridge is used up—replace it" if the display 38 is of the alphanumeric type, or it lights up an LED, for example colored, if the optical display 38 consists of an LED or group of LEDs.

According to a preferred embodiment, the electronic control unit 35 is connected to or is part of the electronic control unit 39 of the testing machine 1, for example by way of a connector 40 (FIG. 1) and it is configured or programmed to disable the operation of the testing machine 1 after the sending of the second warning message, or when the red LED is lit, so as to compel the user to replace the filtering cartridge 15.

The control unit 35/39, in the nonlimiting example illustrated, is connected to a presence sensor 41 for sensing the presence of the filtering cartridge 15, and is designed or programmed to reset the value recorded by the counter 36 as a consequence of the replacement of the filtering cartridge 15. For example, when the testing machine 1 is halted after reaching or exceeding the second predetermined threshold value and the casing 8 is opened to remove the spent filtering cartridge 15, the sensor 41 then detects its removal and the control unit 35/39 resets the hour counter 36; after this, a new filtering cartridge 15 is inserted, which is detected by the sensor 41, and the control unit 39 is enabled to restart the testing machine 1. Obviously, the sensor 41 can be configured to read an optical label or FIR affixed to the filtering cartridge 15 and bearing for example an identification code, by which the control unit 35/39 is able to detect whether the filtering cartridge 15 has been in fact replaced or merely taken out and put back into its place.

Alternatively, it can be ensured that the filtering cartridge 15 is effectively replaced by sending the user a code with the replacement cartridge. In this case, in order to replace the filtering cartridge 15, it is necessary to enter the attached code in the control unit 39 and this will be registered in the system and verified by authorized staff.

Based on what has been described thus far, it is evident that the invention also pertains to a method for hot testing test pieces 2 made of a thermoplastic polymer which is to be tested, said method comprising the steps of immersing the test pieces 2 in a tank 4 full of a heat transfer liquid and of heating the heat transfer liquid for indirectly heating the test pieces 2; and said method furthermore comprising: the step of generating, immediately above the tank 4, an air flow F which can carry away any volatile substances eventually originating from the tank 4; and the step of allowing the air flow F sucked up from above the tank 4 to pass through a filtering cartridge 15 housed removably and in a fluid-tight manner inside a first chamber 10 delimited by a casing 8, which is provided with an inlet opening 11, that faces towards the tank 4 and is arranged flush with or immediately above a perimetral upper edge 6 of the tank 4, and with an outlet opening 14.

The step of allowing the air flow F sucked up from above the tank 4 to pass through the filtering cartridge 15 is effected under conditions of substantially laminar motion and in such a way that the air flow F is made to pass sequentially through at least three filtering elements 18, 19 and 20, which are arranged hydraulically in series with respect to the air flow F and comprise, considered in the direction of the air flow F: an at least grade G2 and preferably grade G4 pre-filter 18; at least one activated carbon filter 19; and a grade H14 HEPA filter 20; the activated carbon filter 19 is interposed between the pre-filter 18 and the HEPA filter 20.

The method of the invention further comprises the steps of:

directly or indirectly measuring the temperature of the heat transfer liquid;
starting the steps of generating, immediately above the tank 4, the air flow F and of allowing the air flow F sucked up from above the tank to pass through the filtering cartridge 15 when a temperature of the heat transfer liquid which is greater than a first predetermined threshold value is measured, to stop the execution of these steps as soon as a temperature of the heat transfer liquid which is lower than the first predetermined threshold value is then measured;
a step of counting the time taken to perform the steps of generating, immediately above the tank 4, the air flow F and of allowing the air flow F sucked up from above the tank 4 to pass through the filtering cartridge 15;
a step of signaling the failure or imminent failure of the filtering cartridge 15, with a request for replacement when the time counted is equal to or greater than, or draws near to, a second predetermined threshold value.

In this way, the intercepting and purification of any volatile substances emitted by the heat transfer liquid is immediate and complete, without the need to involve the fixed installations of the plant where the testing machine 1 is placed; the testing machine 1 and its operating cycle are thus totally independent of the place and position in which it is operating.

The combination of three filtering elements of the indicated type furthermore makes it possible to intercept and eliminate all the pollutants, even any particles of active carbon which have been stripped from the filtering element 19 because of the air flow F. The generating of the air flow F, in addition to carrying away the pollutants and routing them to the filter 15, also makes it possible to lower the temperature of the pollutants, thus increasing the efficiency of the filtering cartridge 15.

Finally, the presence of the control unit 35/39, the hour counter 36 and the sensor 37 makes it possible to use the filtering cartridge 15 only when actually necessary, guaranteeing its efficiency over time. In fact, when the filtering cartridge 15 draws near the moment when it might lose efficiency, after a predetermined number of hours of operation, the control unit 35/39 basically requires the user to replace it.

Thus, all the purposes of the invention are achieved.

Finally, it is clear that modifications and variants can be made to the embodiments described and illustrated here, without thereby leaving the scope of protection of the present invention, as defined in the appended claims. For example, the various described embodiments can be combined in order to provide further solutions.

What is claimed is:

1. A testing machine (1) for carrying out tests on the heat resistance of plastic polymers, said machine comprising:
at least one test station (3) designed to receive at least one test piece (2) made of a plastic polymer which is to be tested;
a tank (4) beneath the at least one test station (3) for selectively receiving the at least one test piece (2);
a heating device (5) housed in the tank or in the vicinity thereof; and
the tank (4) being designed to contain a liquid for transferring heat from the heating device to at least one test piece immersed in the liquid for transferring heat;
characterized in that said machine further comprises a suction and treating device (7) for volatile substances which develop during use from the tank (4), the suction and treating device comprising:
i) a casing (8), which is fixed laterally to a supporting structure (9) above the tank (4) and internally delimits a first chamber (10);

ii) an inlet opening (11) to the first chamber, which is arranged flush with or immediately above a perimetral upper edge (6) of the tank and is made through a lateral wall (12) of the casing facing towards the tank;

iii) a suction fan (13), which is supported by the casing above the first chamber (10) and is connected hydraulically to the first chamber and to an outlet opening (14) made through the casing; and iv) a filtering cartridge (15), which is housed removably inside the first chamber (10) and is hydraulically interposed in a fluid-tight manner between the inlet opening (11) and the suction fan (13).

2. The testing machine as claimed in claim 1, characterized in that the filtering cartridge (15) occupies only in part the first chamber (10), and occludes it immediately above the inlet opening (11), such as the fan (13) is configured to suck an air flow (F) into the first chamber (10) through the inlet opening (11) and is directed towards the outlet opening (14), passes through the filtering cartridge in a prevalently vertical direction; the filtering cartridge (15) comprising at least three filtering elements, which are arranged hydraulically in series with respect to the air flow (F) and comprise, considered in the direction of the air flow: an at least grade G2 and grade G4 pre-filter (18); at least one activated carbon filter (19); and a HEPA filter (20); the activated carbon filter (19) being interposed between the pre-filter (18) and the HEPA filter (20).

3. The testing machine as claimed in claim 1, characterized in that the suction fan (13) is housed inside a second chamber (26) of the casing, said second chamber being arranged above the first chamber (10) and being connected to the first chamber by means of a central hole (27) which is made through a separation bulkhead (28) between the first and the second chamber and forms an integral part of the casing (8); the suction fan (13) being a centrifugal fan configured to axially suck up an air flow (F) from above the tank (4) and through the inlet opening (11) and the filtering cartridge (15) arranged in the first chamber (10) and discharges it radially into the second chamber (26) and towards the outlet opening (14), which is arranged laterally in relation to the second chamber (26) and perpendicular to the inlet opening (11) and which is connected to an environment.

4. The testing machine as claimed in claim 1, characterized in that the supporting structure (9) above the tank (4) is a closed structure which covers the tank and the at least one test station (3) and which is equipped with an access door (30) to the tank and to the at least one test station; the casing (8) of the suction and treating device (7) being supported in a cantilevered manner by a longitudinal end (33) of the supporting structure arranged at a longitudinal end (34) of the tank at which the inlet opening (11) is arranged.

5. The testing machine as claimed in claim 1, characterized in that the suction fan (13), the inlet opening (11) and the filtering cartridge (15) are configured for the suction of an air flow (F) at a predetermined flow rate from immediately above the tank (4).

6. The testing machine as claimed in claim 5, wherein the suction fan (13) is configured to suck said air flow (F) at a predetermined flow rate from immediately above the tank (4) in conditions of laminar motion.

7. The testing machine as claimed in claim 5, characterized in that the filtering cartridge (15) is supported inside the casing (8) by at least four removable pins (22), and is extractable from the casing like a drawer, in a direction perpendicular to a direction of admission of the air flow (F) through the inlet opening (11).

8. The testing machine as claimed in claim 1, characterized in that it comprises a control unit (35,39), an hour counter (36), a temperature sensor (37) arranged in the tank (4) or in the vicinity thereof, and an optical display (38); the control unit (35;39) being configured to start the fan (13) and the hour counter (36) in response to a signal from the temperature sensor (37) indicating that a first predetermined threshold value has been exceeded, and to stop the fan and the hour counter when the temperature detected by the sensor (37) is below the first predetermined threshold value; and to compare a value recorded on the hour counter (36) with a second predetermined threshold value to activate the optical display (38) when the value recorded by the hour counter is equal to a predetermined percentage of the second threshold value and/or is equal to or greater than the second threshold value.

9. The testing machine as claimed in claim 8, characterized in that the testing machine further comprises a presence sensor (41) for sensing the presence of the filtering cartridge (15), the control unit (35,39) being connected to the presence sensor (41) and being configured to reset the value recorded by the hour counter (36) as a consequence of a replacement of a filtering cartridge.

10. A method for hot testing test pieces (2) made of a thermoplastic polymer which is to be tested, said method comprising the steps of immersing the test pieces in a tank (4) full of a heat transfer liquid and of heating the heat transfer liquid for indirectly heating the test pieces; characterized in that said method further comprises the step of generating, immediately above the tank (4), an air flow (F) which can carry away any volatile substances eventually originating from the tank, and the step of allowing the air flow (F) sucked up from above the tank to pass through a filtering cartridge (15) housed removably and in a fluid-tight manner inside a first chamber (10) delimited by a casing (8), which is provided with an inlet opening (11), that faces towards the tank and is arranged flush with or immediately above a perimetral upper edge (6) of the tank, and with an outlet opening (14); the step of allowing the air flow (F) sucked up from above the tank to pass through the filtering cartridge being effected in such a way that the air flow is made to pass sequentially through at least three filtering elements, which are arranged hydraulically in series with respect to the air flow and comprise, considered in the direction of the air flow: an at least grade G2 and grade G4 pre-filter (18); at least one activated carbon filter (19); and a grade H14 HEPA filter (20); the activated carbon filter (19) being interposed between the pre-filter and the HEPA filter.

11. The method as claimed in claim 10, characterized in that it further comprises the steps of:
directly or indirectly measuring the temperature of the heat transfer liquid;
starting the steps of generating, immediately above the tank, said air flow (F) and of allowing air flow sucked up from above the tank to pass through the filtering cartridge (15) when a temperature of the heat transfer liquid which is greater than a first predetermined threshold value is measured, to stop these steps as soon as a temperature of the heat transfer liquid which is lower than the first predetermined threshold value is measured;
a step of counting the time taken to perform the steps of generating, immediately above the tank (4), said air flow and of allowing the air flow (F) sucked up from above the tank to pass through the filtering cartridge; and a step of signalling the failure or imminent failure of the filtering cartridge (15), with a request for replacement when the time counted is equal to or greater than a second predetermined threshold value.

* * * * *